United States Patent [19]

Lee

[11] 4,055,598
[45] Oct. 25, 1977

[54] PROCESS FOR PREPARATION OF UREA AUTOCONDENSATION PRODUCT

[75] Inventor: John M. Lee, Lake Jackson, Tex.

[73] Assignee: The Dow Chemical Company, Midland, Mich.

[21] Appl. No.: 568,095

[22] Filed: Apr. 14, 1975

Related U.S. Application Data

[63] Continuation-in-part of Ser. No. 242,220, April 7, 1972, abandoned, which is a continuation-in-part of Ser. No. 865,211, Oct. 9, 1969, abandoned.

[51] Int. Cl.$^2$ ............................................. C07C 127/24
[52] U.S. Cl. .................................................. 260/553 B
[58] Field of Search ...................................... 260/553 B

[56] References Cited

U.S. PATENT DOCUMENTS

| | | | |
|---|---|---|---|
| 3,862,223 | 1/1975 | Beale, Jr. ........................ | 260/553 B |
| 3,928,438 | 12/1975 | Beale, Jr. et al. ................ | 260/553 B |
| 3,935,260 | 1/1976 | Schlosser ........................ | 260/553 B |

FOREIGN PATENT DOCUMENTS

| | | | |
|---|---|---|---|
| 757,246 | 4/1971 | Belgium | |
| 1,068,693 | 11/1959 | Germany ........................ | 260/553 B |

*Primary Examiner*—Daniel E. Wyman
*Assistant Examiner*—Thomas A. Waltz
*Attorney, Agent, or Firm*—Walter J. Lee

[57] ABSTRACT

A urea-containing reactant is pyrolyzed under controlled temperature conditions of from about 100° to about 150° C. in the presence of an inert hydrocarbon carrier liquid having a boiling point at about the predetermined reaction temperature thereby providing an autocondensation product mass rich in biuret and having a relatively low residual content of unconverted urea. Other autocondensation pyrolyzates, less desired in the product when it is used as a protein supplement for ruminant feeds, are coproduced only in relatively low tolerable amounts.

5 Claims, No Drawings

PROCESS FOR PREPARATION OF UREA AUTOCONDENSATION PRODUCT

CROSS-REFERENCE TO RELATED APPLICATION

The present application is a continuation-in-part of copending application Ser. No. 242,220, filed Apr. 7, 1972, now abandoned, which is a continuation-in-part of application Ser. No. 865,211 filed Oct. 9, 1969, now abandoned.

BACKGROUND OF THE INVENTION

The present invention relates to the preparation of biuret and more particularly is concerned with a pyrolysis process for preparing biuret with high urea conversion.

The preparation of biuret by pyrolysis of urea, as well as other methods, has long been known in the art. Many of these preparations are summarized in an article "Biuret and Related Compounds" published in Chemical Reviews, 56, p. 95–197 (1956). Of the various methods for preparing biuret set forth in this review article it was indicated that although difficulties are present, large scale preparations have been developed based on the pyrolysis of urea.

Olin (U.S. Pat. No. 2,370,065) teaches a process for preparing biuret wherein urea is heated to a temperature above its melting point but below the decomposition temperature of the biuret and by-product ammonia formed by the condensation of urea is swept from the reaction zone with a stream of a hydrocarbon gas. In the practice of the Olin process, the hydrocarbon gas, preferably toluene, is introduced during the reaction period below the surface of the molten urea and the ammonia-hydrocarbon gas mixture rapidly removed from the reaction zone. The ammonia is removed from the resulting hydrocarbon sweep gas-ammonia mixture and the ammonia depleted hydrocarbon gas returned to the reaction zone for removal of further quantities of ammonia.

Harmon (U.S. Pat. No. 2,145,392) teaches a process for preparing biuret by heating urea at a temperature of 130° to 205° C. at a pressure of not substantially greater than 200 mm. of mercury. This allegedly provides a mixture of urea and biuret from which the biuret is subsequently separated.

Kamlet (U.S. Pat. No. 2,768,895) lists a number of references directed to the preparation of biuret by pyrolysis of urea and teaches a process for directly pyrolyzing urea in the absence of a catalyst at a temperature between 120° and 205° C. This effects substantial autocondensation of the urea to produce a mixture of unreacted urea and an admixture of urea autocondensation products, the total mixture consisting of 30 to 70 percent urea with biuret being a predominant component of the autocondensation products. The Kamlet process further includes extracting urea from the resulting product with a selective solvent for urea, e.g. preferably water, to leave a product containing 60 to 90 percent of the admixed autocondensation products with the remainder being urea. The so-extracted product mass is taught to be suitable for use as a protein supplement for ruminant feeds.

Formaini et al. (U.S. Pat. No. 3,057,918) teaches a cyclic process for preparing biuret in which urea is heated at from 135° to 200° C. and the resulting crude pyrolytic product quenched and digested in hot aqueous ammonia until no triuret remains. The liquid mass is then cooled to fractionally crystallize biuret which is removed. The ammonia is stripped from the residual solution whereupon cyanuric acid crystallizes. This solid product is separated from the residual aqueous solution and the solution concentrated by removal of water. The resulting concentrate is recycled with additional urea for subsequent pyrolysis.

Colby (U.S. Pat. No. 2,861,886), Kamlet, (referenced hereinbefore) and other publications attest to the utility of biuret as a feed composition additive for ruminants. This additive provides usable nitrogen to supplement the protein content of feeds from natural sources. Moreover, the use of biuret as a nitrogen supplement is preferred since it is assimilated by ruminant animals at a slower rate than urea-based supplements and consequently avoids the danger of ammonia toxicity to the animal.

While the pyrolysis of urea to yield biuret is well-known in the art, there are many disadvantages associated with such methods. The principal disadvantage lies in the low total conversion of urea to the desired biuret product. Thus, methods wherein urea is directly heated at higher temperatures or for longer periods of time have been employed in attempts to increase the conversion of urea to biuret. It is known, however, that higher reaction temperatures favor the formation of cyanuric acid and a higher total cyanuric acid plus triuret content in the pyrolysis product. Conversely, lower reaction temperatures favor the formation of biuret and a higher biuret content in the pyrolysis product. Moreover, regardless of the prior art direct pyrolysis methods employed, a point is soon reached at which the formed biuret is being converted to higher condensation products faster than more biuret is being formed. Under such conditions, the highest yield of biuret is reached when the pyrolysis product reaches a point at which is contains about 50% biuret. Further heating will give more conversion of urea, but will also cause more of the biuret to become further reacted to form higher condensation products which soon become a solidified mass. Heat transfer through the solidified mass is difficult. If a relatively low temperature (less than 120° C) is employed to avoid higher condensation products, the rate is much too slow to be economically feasible.

In order to thus obtain a ruminant feed product having a high biuret concentration and desirably low concentrations of urea and by-products cyanuric acid and triuret, extraction of the pyrolysis product with water or other solvents to remove a large portion of the urea and byproducts present has thus been necessary in prior art procedures.

In attempting to obviate the problems of the prior art, it was discovered by the applicant and others working with the applicant that the conversion of urea to biuret could be increased by methods wherein the pyrolysis of urea is carried out in certain inert carriers. Such novel methods allow for the close control of the pyrolysis reaction temperature and provide further conversion of urea to biuret while minimizing the build-up of undesired cyanuric acid and triuret by-products. Although such methods provide an improved pyrolysis product containing the desired biuret component in increased concentrations, the applicant and others working with the applicant have discovered that such methods also suffer disadvantages which limit the biuret content of the pyrolysis product that can be obtained to about 55 to about 57 percent. In this respect, as the biuret content of the pyrolysis product is increased and the urea concentration is decreased during the pyrolysis reaction to below 50 percent, the pyrolysis reaction temperature is correspondingly decreased enough to minimize the formation of undesired cyanuric acid and triuret while maintaining the pyrolysis reaction mass in suspension. When the pyrolysis temperature was decreased to about 125° C. and the urea concentration was decreased to below about 40%, usually between about 20 and 40%, it was discovered that the suspended pyrolyzate product would agglomerate, adhering to the reactor walls and agitator blades in sufficient quantities to effectively block further attempts to agitate the reaction mass and maintain the pyrolysis reaction. Much of the solidified reaction mass is lost in difficult recovery efforts from the reactor and the quantity of product that is recovered must be further treated by grinding, milling, etc., procedures to prepare an acceptable product. If the solidified reaction mass is cooled to below about 112° C., further conversion of urea in the mass to biuret can be obtained; however, the rate of conversion is extremely slow and is not economically feasible. The product obtained must also be treated as set forth hereinbefore.

It is a principal object of the present invention to provide a process for production of biuret in high yields by pyrolysis of a urea containing reactant.

It is another object of the present invention to provide a process for production of biuret which assures for good control of reaction conditions and minimizes, if not entirely eliminates, urea reactant losses during the processing.

It is also an object of the present invention to provide a process for preparing biuret by pyrolysis of urea wherein autocondensation by-product formation, particularly cyanuric acid, can be held to a low level.

It is an additional object of the present invention to provide a process which eliminates the need for milling or grinding of the biuret product obtained and provides for the production of biuret in granular or prill form.

It is another object of the present invention to provide a process for preparing a biuret product by pyrolysis of urea in a urea-containing reaction mass wherein there is direct high conversion of urea and a low residual urea level in the product without requiring extraction of such residual urea from the product by a selective solvent, such as water.

These and other objects and advantages of the process of the present invention readily will become apparent from the detailed description presented hereinafter.

GENERAL SUMMARY

In general, the present process comprises heating a urea-containing reactant system in the presence of an inert hydrocarbon carrier liquid at an elevated temperature of from about 100° to about 150° C. which provides for substantial conversion of urea to biuret while simultaneously minimizing the formation of undesirable autocondensation by-products as well as provides for ready removal of evolved by-product ammonia, and recovering the biuret-containing product mass from the carrier liquid.

DESCRIPTION OF PREFERRED EMBODIMENTS

In the actual practice of one preferred embodiment of the present invention, ordinarily a mixture of a urea-containing reactant and inert carrier liquid, hereinafter referred to at times by the term "hydrocarbon", is heated at a temperature of from about 100° C. to about 150° C. and preferably at temperatures from about 115° C. to about 125° C. The heating is carried out for a period of time sufficient to effect a substantial conversion at the temperature employed of the urea contained in the reactant system to biuret while minimizing the formation of other urea autocondensation products such as cyanuric acid and triuret.

The process of the present invention is adapted to be carried out in batch, cyclic, cyclic-batch, or continuous operations. In batch operations, a urea feedstock selected from the group consisting of urea and urea pyrolyzates containing at least about 35 percent by weight urea (such urea pyrolyzates hereinafter referred to at times as "high urea feedstocks") is added under controlled conditions to a predetermined amount of a "seed" of high biuret — low urea pyrolyzate product (hereinafter referred to as a "biuret feedstock" or a "high biuret feedstock") in an inert carrier liquid with agitation. The high urea feedstock is added at rates, usually incrementally or "portionwise", calculated to maintain the urea content of the resulting reaction mass, i.e., urea feedstock and "seed" biuret feedstock, below about 20 percent by weight (based on solids present) at all times during the reaction. The reaction mass thus obtained is maintained within the indicated temperature range set forth hereinbefore for a period of time sufficient to effect substantial conversion of the urea in the reaction mass to biuret. Following this, a slurry comprising hydrocarbon carrier and solid biuret product (hereinafter referred to as the "high biuret product" or "pyrolyzate product") in granular form can be recovered. Usually, the pyrolyzate product has a biuret content of from about 55 to about 85 weight percent or more and a residual urea content of less than 20 weight percent, ordinarily less than about 15 weight percent and preferably less than about 10 weight percent. The solid pyrolyzate product can be separated from the hydrocarbon carrier, usually by conventional liquid — solid separatory procedures. The recovered hydrocarbon carrier is ordinarily recycled for reuse.

To obtain the desirable high biuret product according to the teachings of the present invention, it is critical and essential that the urea content of the reaction mass does not at any time exceed 20 percent by weight (based on solids present). At urea concentrations of about 20 percent and above, the eutectic point of the pyrolyzate mixture is approached or reached and the reaction mass solidifies with resulting loss of suspension and product buildup in and on the reactor vessel and agitating means.

Where optimum urea conversion and practicable conversions periods are desired, a high urea feedstock (of a urea pyrolyzate product) having a urea content of at least about 35 percent by weight is generally employed; feedstocks containing lesser amounts are usually thick, less mobile and difficult to pump. Urea can also be employed in the process of the present invention; however, high urea feedstocks (of a urea pyrolyzate product) having a urea content of from about 35 to about 50 percent or more by weight, a biuret content of from about 40 up to about 55 weight percent, and minor amounts of cyanuric acid and triuret, are preferably employed from the standpoint of economical and practicable urea conversion periods. Longer conversion periods are, of course, necessary where urea or other high urea feedstocks containing urea in excess of about 50 percent by weight are employed; such longer conversion periods generally result in an increased buildup of cyanuric acid and triuret by-products. The "seed" material employed, i.e., the biuret feedstock, ordinarily has a urea content of about 15 weight percent or less, preferably less than about 10 weight percent, the remainder comprising predominantely biuret, usually from about 60 to about 85 weight percent or more, and contains minor amounts of cyanuric acid and triuret. The employment of biuret feedstocks having low levels of urea provides for accelerated feed rates of urea feedstock and thus the conversion of more urea to the desired high biuret product.

The rate of conversion of the urea in the reaction mixture to biuret is dependent upon the reaction temperature employed, increased conversion being obtained at the higher temperatures in the previously stated range, and the concentration of urea in the urea feedstock being added, the rate of urea feedstock addition being regulated so as to maintain the urea concentration of the resulting reaction mass below 20% by weight at all times. The rate of urea conversion can be determined by intermittent product sampling of the reaction mass or by monitoring the evolution rate of by-product ammonia. Generally, when utilizing urea feedstocks containing from about 35 to about 50 percent urea, optimum conversions of urea to biuret are obtained in periods of from about 10 minutes to about 20 hours, usually from about 10 minutes to 10 hours. Lower temperatures in the preferred range set forth hereinbefore are desirably employed to avoid a buildup in the content of undesired cyanuric acid and triuret by-products.

Once the process is underway, a "heel" of the high biuret product obtained can be maintained in the reactor for the next succeeding batch. A cyclic-batch or semi-continuous operation can also be practiced. In such operations, a portion of the high biuret product can be recycled back to the reactor to serve as the initial seed, e.g., the high biuret feedstock, and the fresh high urea feedstock can be added thereto. Within the disclosed temperature range and process period, the actual time employed usually varies inversely with the temperature used. At higher temperatures, the conversion rate of urea to biuret is increased but this is accompanied by an acceleration in the rate of formation of other urea autocondensation products, e.g., triuret, ammelide and cyanuric acid, which are not desired when the biuret product is to be used as a protein supplement ruminant feed additive.

Further, the foregoing process is characterized as being capable of being carried out continuously to give high biuret products comprising less than 20 percent by weight urea and only minor amounts of cyanuric acid and triuret by-products. Thus, the urea feedstock is continuously introduced or metered into a reactor containing a slurry of liquid hydrocarbon and predetermined amount of high biuret feedstock and mixed therewith. The high biuret slurry is heated and is maintained at a temperature of from about 100° to about 150° C., preferably from about 115° to about 125° C. Alternatively, the hydrocarbon carrier and urea feedstock can be mixed to the predetermined reaction temperature and then introduced into the reactor and mixed with the high biuret slurry. The resulting reaction mass is maintained at the indicated temperature and is carried out at a throughput rate and in a reaction mixture volume to provide an apparent average residence time for a given unit of urea feedstock of at least about 10 minutes, or preferably, sufficient to effect a substantial conversion of the urea to biuret at the temperature employed. Based on the quantity of biuret feedstock initially present and the urea content of the urea feedstock, the through-put rate is calculated to maintain the total urea content of the reaction mass solids below about 20 percent by weight. Generally, depending upon the reactor size, the quantity of high biuret feedstock and hydrocarbon carrier initially in the reactor, the urea content and rate of the urea feedstock being introduced and the concentration of urea (below 20 percent) desired in the high biuret product, good conversion results of urea are obtained at apparent through-put rates per given unit of urea feedstock ranging fromm about 10 minutes to about 50 hours or more.

When carrying out the continuous process, a slurry of hydrocarbon liquid and high biuret product is continuously withdrawn from the reactor at a rate commensurate with the rate of introduction of the urea feedstock-hydrocarbon slurry. Additional hydrocarbon liquid is also continuously introduced when the urea feedstock is separately introduced so as to maintain a nearly constant volume in the reactor. The withdrawn product slurry is treated according to procedures set forth hereinbefore and the granular high biuret product obtained.

The relative quantities of total urea reaction mass (i.e. urea and its pyrolyzate products) and hydrocarbon to be employed can be varied. For optimum efficiency in handling, heat consumption, reactant contact, product recovery, etc. the relative proportions of the urea-containing portion of the mass:hydrocarbon liquid range on a weight basis from about 5:95 to about 60:40. Usually, the mixture contains from about 20 to about 45 weight percent of the urea-containing moiety. At hydrocarbon contents of less than about 50 weight percent stirring difficulties sometimes may be encountered. With reaction mixtures containing excessively large amounts of the hydrocarbon, i.e. much greater than above 90 percent, increased expense, e.g. heating and handling costs, can be encountered without providing any marked increase in product yield of process efficiency.

Conveniently, the high urea feedstock is introduced into a slurry of liquid hydrocarbon and high biuret feedstock which previously has been heated and is maintained at a predetermined temperature. Alternatively, hydrocarbon and high urea feedstock can be mixed and the resultant mixture heated to the predetermined reaction temperature. As indicated hereinbefore, batch, cyclic, cyclic-batch, or continuous operations can be employed.

Hydrocarbons suitable for use as carrier liquids in the process of the present invention are those compounds which have a density less than that of the reactants, i.e., the urea feedstock, the biuret feedstock, and the resulting reaction mixture thereof and which have an observed boiling point at the reaction temperature and pressure conditions employed and preferably have a freezing or gelling point below about 20° C. These hydrocarbons should be substantially a non-solvent for urea and its autocondensation pyrolyzate products and be inert to these substances as well as be inert to the ammonia evolved during the process.

Ordinarily hydrocarbons having a normal boiling point at about the predetermined reaction temperature are employed. The use of such a carrier liquid at its boiling point virtually eliminates the need for a separate inert gas sparge to remove evolved ammonia by-product gas from the reaction mixture since the vapors from this liquid serve to carry off this by-product. Once having been removed from the reaction zone this carrier liquid can be condensed, the ammonia separated therefrom and both be recovered. Conveniently, the condensed carrier liquid is recycled in closed circuit directly back to the pyrolyzate reactor; this substantially reduces the need for make-up carrier liquid in the system. Alternatively, all of a portion of the recovered liquid can be vaporized and the vapors introduced directly into the reactor thereby serving as a sparge for ammonia removal. On the return cycle, high urea feedstock can be introduced in controlled amounts into the hydrocarbon and the resulting slurry fed to the reactor.

In actual operations, the reflux temperature of the carrier liquid can be changed from its normal boiling point through use of a reduced or elevated pressure on the system. This can offer advantage in some instances. For example, a carrier liquid can be selected which has a normal boiling point higher than the reaction temperatures disclosed. The pressure of the system can be controllably reduced below atmospheric pressure until the observed boiling point of the liquid is that of the predetermined reaction temperature. By use of the partial vacuum, the gaseous vapors are actually pulled from the reaction zone thereby further facilitating by-product ammonia removal from the system.

Conversely, the boiling point of hydrocarbon carrier liquid can be raised a predetermined amount by controllably applying a superatmospheric pressure to the system.

Boiling point control of the carrier liquid also can be achieved by use of mixtures of lower and higher boiling components.

Operable compounds preferably employed as carrier liquids are the saturated branched-chain and straight-chain hydrocarbons of the alkane series having from 8 to 12 carbon atoms. Alkanes of lower or higher carbon contents can be employed through use of suitable system pressure control or in blends of high and low boiling components.

In actual practice it has been observed that with the branched-chain hydrocarbon carrier liquids, the alkane can be more readily substantially completely removed from the pyrolyzate product; accordingly, the branched-chain alkanes usually are employed. Although I do not intend to be bound by any particular theory or mode of operation, it is believed that this phenomenon results from the fact that clathrates can form between urea and the straight-chain alkanes while these apparently do not form with the branched-chain alkanes.

Representative examples of hydrocarbon carrier liquids suitable for use in the practice of the present invention are presented in Table I. These are not meant to be inclusive or limiting but are only to illustrate operable carrier liquids.

Table I

| Compound | Structural Formula | B.P. °C. 760 mm | B.P. °C. 100 mm |
|---|---|---|---|
| n-octane | $CH_3(CH_2)_6CH_3$ | 126 | 66 |
| 3-methylheptane | $CH_3CH_2CH(CH_3)(CH_2)_3CH_3$ | 119 | 60 |
| 3-ethylhexane | $CH_3CH_2CH(C_2H_5)(CH_2)_2CH_3$ | 119 | 60 |
| 2,5-dimethylhexane | $CH_3CH(CH_3)(CH_2)_2CH(CH_3)CH_3$ | 109 | 50 |
| 3-ethyl-3-methylpentane | $CH_3CH_2C(CH_3)(C_2H_5)CH_2CH_3$ | 118 | 57 |
| 2,2,4-trimethylpentane | $CH_3C(CH_3)_2CH_2CH(CH_3)CH_3$ | 99 | 41 |
| n-nonane | $CH_3(CH_2)_7CH_3$ | 151 | 88 |
| 2-methyloctane | $CH_3CH(CH_3)(CH_2)_5CH_3$ | 143 | 81 |
| 3-ethylheptane | $CH_3CH_2CH(C_2H_5)(CH_2)_3CH_3$ | 143 | 80 |
| 2,4-dimethylheptane | $CH_3CH(CH_3)CH_2CH(CH_3)(CH_2)_2CH_3$ | 136 | 71 |
| 3,3,4-trimethylhexane | $CH_3CH_2C(CH_3)_2CH(CH_3)CH_2CH_3$ | 140 | 77 |
| 4-propylheptane | $CH_3(CH_2)_2CH(C_3H_7)(CH_2)_2CH_3$ | 162 | 96 |
| 2,2,4,5-tetramethylhexane | $CH_3C(CH_3)_2CH_2CH(CH_3)CH(CH_3)CH_3$ | 148 | 83 |
| n-undecane | $CH_3(CH_2)_9CH_3$ | 196 | 128 |
| n-dodecane | $CH_3(CH_2)_{10}CH_3$ | 216 | 146 |

The use of the hydrocarbon medium as a carrier liquid has been found to provide at a given temperature an increased rate of conversion of urea in the feedstock to biuret thereby reducing the reaction time. This in turn reduces the formation of other urea autocondensation products. Additionally, as stated hereinbefore, the carrier liquid provides for ready escape of by-product ammonia without the need for large volumes of other sparge gases from the reaction mass as well as substantially eliminates loss of the urea reactant since any entrained urea readily can be removed therefrom. Another advantage of the carrier is that it acts as a heat transfer medium thereby providing for close control of the reaction temperature; this is particularly effective in minimizing cyanuric acid formation. A further unexpected advantage is the fact that the carrier liquid serves to protect the surfaces of reactors and material handling equipment from direct contact with reaction products which could have a corrosive affect thereon.

Although no additional sparging or flushing of the reaction system with additional inert gas such as nitrogen, argon, lower boiling hydrocarbons (i.e. methane, ethane, propanes, butanes, pentanes, hexanes, or heptanes, for example) is required, is desired, a flow of such a purge gas through the reaction mass can be maintained to provide a positive influence on the evolved ammonia and vapors of carrier liquid to assist in their removal from the heated reaction zone.

The high urea feedstock component for use in the present process can be prepared by a variety of means. For example, urea can be partially pyrolyzed by heating at a temperature of from about 150° to about 210° C., preferably at from about 160° to about 185° C. and maintained within this temperature range for a period of from about 10 minutes to about 6 hours followed by staged cooling, either in a stepwise progression or continuously to a temperature of from about 110° to about 130° for a period sufficient to provide a pyrolysis product having a biuret content or up to about 55 weight percent, the remainder being predominantly urea.

The high urea feedstock also can be prepared by pyrolyzing urea in a falling film reactor to provide a pyrolyzate having a biuret content of up to about 40 weight percent or more. In such a process a molten urea feedstock or aqueous urea solution is introduced at a flow rate into a falling film reactor maintained at a temperature to provide a pyrolyzate product exit temperature of from about 180° to about 240° C. and preferably from about 195° to about 230° C. Ordinarily the urea feed material feed rate is from about 180 to about 600 pounds of actual urea compound/hour/foot of reactor periphery (lb./hr./ft.). Preferably, a flow rate of from about 430 to about 520lb./hr./ft. is employed with the reactor temperature being maintained to produce a pyrolyzate product having an exit temperature of from about 215° to about 225° C.

In another process a mixture of urea and a high boiling inert carrier liquid, e.g. a petroleum oil or vegetable oil is heated, preferably simultaneously sparged with an inert gas, at a temperature of from about 150° to about 210° C., preferably at from about 160° to about 180° C. for a period of from about 10 minutes to about 2 hours, ordinarily at from about 30 minutes to about 1 hours. Following the initial processing, the temperature of the reaction mass is progressively lowered, either stepwise or continuously, to a final temperature within the range of from about 120° to about 135° C. and maintained at this level until the biuret content of the product reaches a maximum of about 55 percent.

The high urea feedstock can also be a partially pyrolyzed autocondensation product produced by any of a variety of conventional art processes of the type described in the forepart of the present specification.

It also should be understood that a high urea feedstock for use in the present process also can be prepared by subjecting urea to a combination of the foregoing processes to obtain a product of a predetermined urea and biuret content. To illustrate, a urea feed can be rapidly partially pyrolyzed in a falling film reactor to give a product containing 20 to 40 percent biuret and the product can then be fed to a continuous process reactor maintained at a temperature of from about 125° to about 180° C., preferably about 132° to about 140° C. wherein the biuret content can be increased, the said continuous process being carried out by continuously feeding the said product into the reactor and continuously withdrawing a product having a biuret content of up to about 57 percent, the remainder being predominantly urea.

This latter pyrolyzate can be recovered and stored prior to use in the process of the present invention or it can be added directly, or as a slurry, to the reactor for preparing the high biuret — low urea pyrolyzate product resulting from the instant invention.

The high-biuret feedstock employed as "seed" material in the process of the present invention can be obtained by extracting prior art urea pyrolysis products with water to remove mainly urea, which has a relatively high solubility in water. This water extraction leaves a portion of the urea pyrolysis product with an increased content of materials having lower water solubility, e.g., biuret, for use as a "seed" material in the process of the present invention.

The following Examples will serve to further illustrate the present invention but are not meant to limit it thereto.

EXAMPLE 1

A 250 ml. 3-neck flask, with four creases pressed into the sides to produce the effect of baffles, was used as a reactor. An air motor driven paddle stirrer equipped with a ground glass seal was attached through one of the pot openings. A helices packed column with cold finger head was attached to another opening and the third was plugged but used as the opening for adding fresh feed and hydrocarbon carrier liquid. The reactor was heated by an electric mantle and the cold finger head was operated on a refrigeration system to maintain 4° C. in the condenser. Effluent gases and vapors were vented through a trap and standard acid solution.

About 124 grams of an isoparaffinic hydrocarbon fraction sold under the Trademark of Isopar E ® and primarily consisting of branched-chain alkanes containing 8 carbon atoms was charged into the reactor along with about 47 grams is an isooctane reference fuel (50 percent distilled at 100° C). This provided a liquid hydrocarbon blend which had an atmospheric boiling point of 115° C.

Twenty grams of a high biuret feedstock resulting from pyrolysis of urea was introduced into the pot as a "seed" and the reaction mass brought to reflux. The seed material on a weight basis analyzed: urea — 9.3 percent; biuret — 67.3 percent; cyanuric acid — 10.7 percent; triuret — 12.7 percent (by difference).

About 3 grams of a high urea feedstock (urea 32.9 percent; biuret — 51.2 percent; cyanuric acid — 12.5 percent; triuret — 3.4 percent (by difference)) was added to the reactor and the mass heated for three hours, subsequent additions of 4.5 grams of the high urea feedstock followed by two hours reaction period, 5 grams reactant with a two hour reaction period and 5.5 grams of urea feed with a final reaction period of 2.5 hours. During the processing the temperature of the reaction mass rose to 117° C.

A small flow of nitrogen, about 2 cubic centimeters/minute introduced between the condenser outlet and the trap and acid scrubber was maintained for the entire process time. This prevented acid solution from being drawn back into the reactor as ammonia was absorbed therein.

During the reaction period a total of 250 ml. of 0.1 Normal hydrochloric acid was neutralized by the evolved ammonia. The product was removed from the reactor and separated from the hydrocarbon carrier liquid by filtering through a glass frit under a reduced pressure. About 31 grams of a solid granular, substantially dust free product was recovered. This was heated to about 104° to about 110° C. for a period of about 10 minutes to dry and remove any absorbed carrier liquid therefrom. The dried product weighed about 30 grams.

Wet chemical analysis of the pyrolyzate product showed the composition to be: urea — 10.8 percent; biuret — 62.8 percent; cyanuric acid — 15.5 percent; triuret — 10.9 percent (by difference). Nuclear magnetic resonance analysis showed a hydrocarbon of 0.25 percent as octanes.

EXAMPLE 2

The apparatus described in Example 1 was modified by changing the reflux column to a Vigreux type unit.

About 124 grams of the isoparaffinic hydrocarbon and 15 grams of the high biuret feedstock "seed" described in Example 1 were placed into the reactor and heated to reflux, the reactor temperature being 124° C. Fifteen grams of the high urea feedstock described in Example 1 was added incrementally to the heated slurry in the reactor over a period of 4.5 hours.

The pyrolyzate product was recovered and dried. Wet chemical analysis indicated: urea — 13.8 percent; biuret — 63.0 percent; cyanuric acid — 14.7 percent; triuret — 9.5 percent (by difference).

EXAMPLE 3

A high biuret product prepared by following the procedure and using the same reactor and process conditions described in Example 2 was prepared. This pyrolyzate product upon analysis was found to contain: urea — 8.7 percent; biuret — 68.9 percent; cyanuric acid and other titratable materials — 13.4 percent; other autocondensation products and residual hydrocarbon — 10.0 percent (by difference).

About 45.5 grams of this product and 100 grams of isoparaffin hydrocarbon (substantially a mixture of branched-chain octanes) were mixed in the reactor and heated to reflux (reactor temperature = 124° C.; overhead vapor temperature = 117° C.).

A high urea feedstock (50 percent biuret, 36 percent urea, 8.5 percent cyanuric acid, 5.5 percent other compounds (by difference) was added in 2.5 gram increments each 30 minutes until a total of 42.5 grams of crude feed had been added. A total of 8.5 hours at reflux temperature was used. The reaction mixture was cooled and filtered and the recovered solid granular pyrolyzate product was analyzed using several analytical techniques as follows:

| Compound | Wt. % by Urease Method | Wt. % by Colorimetric Method | Wt. % by Polarographic Method |
|---|---|---|---|
| Biuret | — | 74.5 | 76.0 |
| Urea | 10.5 | — | — |
| Titratables (incl. cyanuric acid) | — | 13.0 | — |

Into 101 grams of the hydrocarbon carrier liquid (55 grams recycled from preceding run and 46 grams of fresh hydrocarbon) was added 35 grams of the above product. The mixture was brought to reflux temperature (pot temperature of 124° C.) and high urea feedstock (urea — 9.3 percent; biuret — 67.3 percent; cyanuric acid — 10.7 percent; triuret — 12.7 percent (by difference)), were brought to reflux, i.e. pot temperature of 124° C., and incremental additions of a high urea feedstock (urea — 32.9 percent; biuret — 51.2 percent; cyanuric acid — 12.5 percent; triuret — 3.4 percent (by difference)) were made thereto.

The schedule of the urea feedstock addition was as follows: initial addition of 5 grams followed at 30 minute intervals with 2.5 gram additions until a total of 15 grams of feedstock had been added. This produced a reaction mixture having a urea reaction mass concentration of about 44 weight percent. No stirring difficulties were encountered.

Analysis of the biuret product recovered from the reaction mixture indicated: urea — 12.2 percent; biuret — 65.7 percent; cyanuric acid — 11.9 percent; triuret 10.2 percent.

EXAMPLE 5

A study was made to follow the effect of urea concentration in the feed on reaction mix characteristics.

Using the same reactor equipment, process conditions, carrier liquid, high biuret feedstock "seed" (urea content — 9.3 percent) and high urea feedstock (urea content — 32.9 percent) as set forth in Example 4, about 125 grams of the carrier liquid and 20 grams of seed were brought to reflux (124° C. reactor temperature) and the high urea feedstock added in increments over a short time interval until the solids in the reaction mass started to become irregularly cemented together. This occurred when the urea concentration in the mass increased to about 18%. Table III, which follows, summarizes the results of this study:

Table III

| Urea Addition No. | Elapsed Reaction Time (min.) | Urea Feedstock Increment Added (g.) | Total Urea Feedstock Introduced (g.) | Total Urea In Mix (g.) | Urea Content of Mix (% of Total Solids in Reaction Mass) |
|---|---|---|---|---|---|
| 1 | 0 | 3 | 3 | 2.86 | 12.4 |
| 2 | 7 | 1.5 | 4.5 | 3.36 | 13.7 |
| 3 | 9 | 1.5 | 6 | 3.86 | 14.85 |
| 4 | 11 | 1.5 | 7.5 | 4.36 | 15.9 |
| 5 | 13 | 2.0 | 9.5 | 5.02 | 17.0 |
| 6 | 15 | 2.1 | 11.6 | 5.71 | 18.05 | stock of the same composition used in the initial preparation was added in 2.5 gram increments every 30 minutes until a total of 45 grams of high urea feedstock had been added. The slurry was 44 percent solids (calculated) at this point and the particles were well suspended (no agglomeration). The product slurry was filtered after cooling to separate the high biuret product from the carrier liquid. The product analyzed as follows:

| Compound | Percent by Weight |
|---|---|
| Biuret | 71.5 (colorimetric method) [73.0 (polarographic method)]* |
| Urea | 11.3 (urease method) |
| Cyanuric Acid (and other Titratables) | 12.6 (titration) |

*separate analysis made for comparative purposes.

EXAMPLE 4

Using the apparatus and carrier liquid described in Example 2, about 100 grams of the branched-chain hydrocarbon and 65 grams of a prilled high biuret seed For each in expression, since no intermediate analyzes were made on the product, it is assumed in the calculations that all of the urea introduced is still present in the reaction mixture at the time of each subsequent urea reactant addition. In actuality, some biuret product is being formed during this reaction period as is evidenced from the product analysis taken after the last urea feedstock addition and following product separation and recovery from the carrier liquid. Product analysis for the principal components showed: urea — 16.15 percent; biuret — 63.90 percent; cyanuric acid — 10.47 percent.

The resulting product granules were of an irregular, popcorn like appearance. The product material did not stick to the reactor walls or build up on the stirrer.

A comparative screen analysis of the product, the high biuret feedstock seed and the high urea feedstock follows:

Urea Feedstock — 100 percent passed through a 14 mesh U.S. Standard Sieve

"seed" — 99.3 percent passed through a 14 mesh U.S. Standard Sieve

EXAMPLE 6

Urea at a flow rate of about 596 pounds per hour is fed continuously into a heated, jacketed reactor equipped with an agitator and maintained at about 140° C. The urea is held in this first reactor for a period sufficient to melt the mass and provide an initial partial pyrolysis; the reaction mass is continuously sparged with nitrogen at a flow rate of 250 cubic feed per minute.

The nitrogen sparge gas is found to contain urea (18 pounds/hour) and 64 pounds per hour of ammonia. This effluent is sent to a scrubber to remove the ammonia and entrained urea therefrom. The pyrolysis product from the first reactor nominally contains on a weight basis: 50 percent biuret, 38 percent urea, 8 percent cyanuric acid and 4 percent other urea autocondensation products.

The pyrolysis product, i.e., a high urea feedstock, is removed from the first reactor at a flow rate of about 514 pounds per hour and is dispersed in sufficient isooctane to form about a 20 percent by weight slurry. This slurry (at a rate of about 2570/lbs/hour) is transported to a second reactor containing a "seed" biuret feedstock (nominally containing about 68 percent biuret, 12 percent urea, the remainder comprising mainly cyanuric acid and triuret), about 15,000 pounds, and isooctane carrier medium (normal boiling point of about 119° C.) in sufficient quantity to give a total slurry volume in the reactor of about 75,000 pounds. The slurry in the reactor is maintained at about 120° C. and isooctane vapors are sparged through the system at a flow rate of about 12,500 pounds per hours.

A slurry (20 percent solids) containing a high biuret pyrolyzate product is continuously removed from the reactor at a rate of about 2,450 pounds per hours. The solid granular high biuret product is separated from the hydrocarbon liquid by decantation and dried. The product obtained nominally contains on a weight basis 68 percent biuret, 12 percent urea, 11 percent cyanuric acid, and 9 percent other urea autocondensation products.

By-product ammonia evolved during this latter stage of reaction is effectively removed from the second reactor by vapors of isooctane which serve as a sparge gas. The ammonia is removed from the hydrocarbon usually by condensing the isooctane. At least a portion of the isooctane recovered either from the ammonia take-off step or from separation of the high biuret pyrolyzate from the product slurry, is vaporized and this gaseous mass recycled to the second reactor where it serves as sparge gas. It is a principal advantage of the present process that the need for large volumes of a secondary, inert sparge or purge gas for ammonia removal are not required.

In a manner similar to that described for the foregoing Examples, other carrier liquids as set forth hereinbefore are employed to provide a reaction mixture wherein the liquid hydrocarbon carrier has an observed boiling point of from about 100° C. to about 150° C. to prepare the high biuret — low urea pyrolyzate product resulting from the practice of the present invention.

In actual operations, for example, n-nonane, 2-methyloctane, 2,4-dimethylpentane, 3-ethyl-2-methylpentane, 2,5-dimethylhexane, 2,2,4-trimethylpentane and the like hydrocarbons having a normal boiling point between about 100° and 150° C. are used in operations carried out under reflux at atmospheric pressure. Similarly, n-undecane, n-dodecane and 4-propylheptane, for example, are employed in a reaction system maintained at an absolute pressure of about 100 millimeters mercury.

The above and other hydrocarbons as defined herein are used along or in blends to provide a carrier liquid having an observed boiling point at about the predetermined reaction temperature.

The particular carrier liquid to be employed in a given operation is governed by the process conditions, in particular the desired operating pressure and temperature, to be encountered. Having determined what reaction conditions are to be used, the actual selection of a carrier liquid is within the knowledge of one skilled in the art.

I claim:

1. A process in which urea is pyrolytically converted to biuret, said process consisting of
    dispersing, with agitation in an inert hydrocarbon carrier, a seed material consisting of a urea pyrolyzate product essentially containing less than about 15 weight percent urea, about 60 to about 85 weight percent of biuret, and minor amounts of other urea condensation products,
    adding to the so-dispersed seed material, with agitation, a feedstock material consisting of a urea pyrolyzate product essentially containing about 35 weight percent or more or urea, a biuret content of up to about 55 weight percent, and minor amounts of other urea condensation products,
    wherein the feedstock material is added in an amount that the total urea content of the combined seed and feedstock does not exceed 20 weight percent,
    the ratio of the combined seed and feedstock to hydrocarbon carrier being in the range of about 5:95 to about 60:40 by weight,
    heating, with agitation, the mixture of seed and feedstock dispersed in said carrier at a temperature in the range of about 100° C to about 150° C for a period of time of from about 10 minutes to about 8 hours to cause pyrolysis of the urea,
    and recovering from said carrier a urea pyrolyzate product containing less than about 15 weight percent urea, 60 to about 85 weight percent biuret, and minor amounts of other urea condensation products,
    wherein the said inert hydrocarbon carrier is substantially a non-solvent for, and is substantially inert to, ammonia, urea and autocondensation pyrolysis products of urea, said carrier comprising at least one of those compounds selected from the group consisting of saturated branched-chain and straight-chain hydrocarbons of the alkane series having from 8 to 12 carbon atoms.

2. The process as defined in claim 1 wherein the reaction mixture is maintained at from about 115° C to about 125° C.

3. The process as defined in claim 1 wherein the inert hydrocarbon carrier comprises branched-chain octanes.

4. The process as defined in claim 1 wherein said feedstock material consists of a urea pyrolyzate product containing about 32.9 to about 36 weight percent urea and about 50 to about 51.2 percent biuret with the remainder being other urea pyrolyzate products.

5. The process of claim 1 wherein urea pyrolyzate product having a urea content of less than about 15 weight percent and a biuret content of at least about 60 weight percent, is removed at a rate commensurate with the addition of feedstock material, while maintaining the total urea content of the combined feedstock and seed at not more than about 20 weight percent and while maintaining the prescribed weight ratio of combined seed and feedstock/hydrocarbon carrier by the addition of requisite amounts of said carrier.

* * * * *

UNITED STATES PATENT AND TRADEMARK OFFICE
CERTIFICATE OF CORRECTION

PATENT NO. : 4,055,598  
DATED : October 25, 1977  
INVENTOR(S) : John M. Lee

It is certified that error appears in the above-identified patent and that said Letters Patent are hereby corrected as shown below:

Col. 2, Line 38 the word "is" between which and contains should be--it.

Col. 6, Line 16, the word "fromm" should be--from.

Col. 6, Line 43, the word "of" should be--or.

Col. 6, Line 45, the word--a--should be inserted between "of" and "liquid".

Col. 7, Line 10, the word "of" between the words "all" and "a" should be--or.

Col. 8, Line 43, the word "is" between "required" and "desired" should be--if.

Col. 8, Line 58, the word "or" should be--of.

Col. 10, Line 8, the word "is" should be--of.

Col. 10, Line 64, the number "9.5" should be--8.5.

UNITED STATES PATENT AND TRADEMARK OFFICE
CERTIFICATE OF CORRECTION

PATENT NO. : 4,055,598

DATED : October 25, 1977

INVENTOR(S) : John M. Lee

It is certified that error appears in the above-identified patent and that said Letters Patent are hereby corrected as shown below:

Col. 12, Line 27, the word--the--should be inserted between the words "of" and "seed".

Col. 12, Line 47, the word "each" should be--ease, and the word "analyzes" should be--analyses.

Col. 13, Line 11, the word "feed" should be--feet.

Col. 14, Line 4, the word "along" should be--alone.

Col. 14, Line 24, the word "or" between the words "more" and "urea" should be--of.

Col. 14, Line 39, the word--about--should be inserted after "urea," and "60".

Signed and Sealed this

Eleventh Day of April 1978

[SEAL]

Attest:

RUTH C. MASON
Attesting Officer

LUTRELLE F. PARKER
Acting Commissioner of Patents and Trademarks